United States Patent [19]

Eckenhoff

[11] Patent Number: 4,966,767
[45] Date of Patent: Oct. 30, 1990

[54] RUMINANT DISPENSING DEVICE COMPRISING AGENT DISPLACEMENT MEMBER

[75] Inventor: James B. Eckenhoff, Los Altos, Calif.

[73] Assignee: ALZA Corporation, Palo Alto, Calif.

[21] Appl. No.: 327,935

[22] Filed: Mar. 23, 1989

Related U.S. Application Data

[60] Division of Ser. No. 126,460, Nov. 27, 1987, Pat. No. 4,871,544, which is a division of Ser. No. 42,197, Apr. 24, 1987, which is a continuation of Ser. No. 766,456, Aug. 16, 1985, Pat. No. 4,704,118.

[51] Int. Cl.[5] .............................................. A23K 1/18
[52] U.S. Cl. ..................................... 424/438; 424/473
[58] Field of Search ............................. 424/438, 473; 604/892.1

[56] References Cited

U.S. PATENT DOCUMENTS

| | | | |
|---|---|---|---|
| 2,340,037 | 1/1944 | Zipper | 167/83 |
| 3,594,469 | 7/1971 | Whitehead et al. | 424/22 |
| 3,732,865 | 5/1973 | Higuchi et al. | 128/260 |
| 3,760,804 | 9/1973 | Higuchi et al. | 128/260 |
| 3,769,805 | 9/1973 | Higuchi | 128/260 |
| 3,844,285 | 10/1974 | Laby | 128/260 |
| 3,845,770 | 11/1974 | Theeuwes et al. | 128/260 |
| 3,929,132 | 12/1975 | Higuchi | 128/260 |
| 3,995,631 | 12/1976 | Higuchi et al. | 128/260 |
| 3,995,632 | 12/1976 | Nakano et al. | 128/260 |
| 4,034,756 | 7/1976 | Higuchi et al. | 128/260 |
| 4,058,122 | 11/1977 | Theeuwes | 424/468 |
| 4,088,864 | 4/1978 | Theeuwes et al. | 219/121 |
| 4,111,202 | 9/1978 | Theeuwes | 128/260 |
| 4,178,361 | 12/1979 | Cohen et al. | 424/22 |
| 4,196,187 | 4/1980 | Dannelly et al. | 424/21 |
| 4,200,098 | 4/1980 | Ayer et al. | 128/260 |
| 4,228,149 | 10/1980 | Brewer et al. | 424/14 |
| 4,235,236 | 11/1980 | Theeuwes | 128/260 |
| 4,285,987 | 8/1981 | Ayer et al. | 427/3 |
| 4,298,003 | 11/1981 | Theeuwes et al. | 604/892 |
| 4,300,558 | 11/1982 | Eckenhoff et al. | 604/892 |
| 4,326,522 | 4/1982 | Guerrero et al. | 424/438 |
| 4,327,725 | 5/1982 | Cortese et al. | 604/893 |
| 4,381,780 | 5/1983 | Holloway | 424/438 |
| 4,468,220 | 8/1984 | Willbanks | 604/890 |
| 4,595,583 | 1/1986 | Eckenhoff et al. | 604/892 |
| 4,612,186 | 9/1986 | Eckenhoff et al. | 604/890 |
| 4,627,971 | 12/1986 | Ayer | 424/468 |
| 4,692,336 | 9/1987 | Eckenhoff | 424/468 |
| 4,717,568 | 1/1988 | Eckenhoff | 424/468 |

FOREIGN PATENT DOCUMENTS

| | | | |
|---|---|---|---|
| 19250 | 3/1972 | Australia . | |
| 2729068 | 11/1979 | Fed. Rep. of Germany . | |
| 1540258 | 9/1968 | France | 125/424 |
| 2122086 | 1/1984 | United Kingdom . | |

*Primary Examiner*—Cashion, Jr. Merrell C.
*Assistant Examiner*—Leon R. Horne
*Attorney, Agent, or Firm*—Paul L. Sabatine; Edward L. Mandell; Steven F. Stone

[57] ABSTRACT

A dispensing device is disclosed for delivering a beneficial agent. The device comprises (1) a housing defining an internal space, (2) an expandable composition comprising a dense member in the space, (3) a composition comrising a beneficial agent and a non-toxic heat responsive carrier in the space, and (4) a passageway in the housing for delivering the beneficial agent from the dispensing device.

9 Claims, 1 Drawing Sheet

RUMINANT DISPENSING DEVICE COMPRISING AGENT DISPLACEMENT MEMBER

CROSS-REFERENCE TO RELATED APPLICATIONS

This application is a division of U.S. patent application Ser. No. 07/126,460 filed Nov. 27, 1987 now U.S. Pat. No. 4,871,544 issued Oct. 3, 1989 which application Ser. No. 07/126,460 is a division of U.S. application Ser. No. 07/042,197 filed Apr. 24, 1987, which Ser. No. 07/042,197 is a continuation of U.S. application Ser. No. 06/766,456 filed Aug. 16, 1985, now U.S. Pat. No. 4,704,118 issued Nov. 3, 1987. This application is co-pending U.S. application Ser. No. 07/126,079 filed Nov. 27, 1987. These applications are incorporated herein by reference and benefit is claimed of their filing dates. These applications are assigned to ALZA Corporation of Palo Alto, Calif.

FIELD OF THE INVENTION

This invention pertains to both a novel and useful dispensing device. More particularly, the invention relates to a dispensing device comprising a wall surrounding an internal lumen containing (1) a thermo-responsive beneficial agent formulation and (2) an expandable delivery means containing weight means. The thermo-responsive formulation and the delivery means perform in concert for dispensing a beneficial agent through passageway means to an animal over a prolonged period of time.

BACKGROUND OF THE INVENTION

Ruminant animals, including cattle, sheep, giraffe, deer, goat, bison and camels, and more particularly cattle and sheep, comprise an important groups of animals that require periodic administration of medicines and nutrients. These medicines and nutrients are administered for the treatment and alleviation of various medical and infectious related conditions and generally for better health. Ruminants have a complex three or four compartment stomach. The rumen, the largest of the stomach compartments, serves as an important location for receiving and passing medicines and nutrients into other compartments, including the abomasum and the intestine. Presently, ruminants are treated by repeated administrations of medicines and nutrients at frequent time intervals. This form of treatment is inconvenient and expensive, and it does not lend itself to good reliable therapy. Additionally, medicines and nutrients are administered orally in the form of a bolus to ruminants. However, bolus form of therapy, like the repeated dose mode of administration, does not lend itself to widely-practiced and acceptable therapy. That is, ruminants regurgitate what they swallow, they chew their cuds, and they spit out conventional boluses quickly after administration.

There is, therefore, in view of the above presentation, a pressing need for a therapeutic delivery system for use in ruminant therapy that will, after a single administration, efficiently dispense medicines and nutrients over a prolonged period of time. There also is a pressing need for a therapeutic delivery system for prolonged releasing of a medicine or a nutrient at a controlled rate in the rumen, by a delivery system that is swallowed easily by the ruminant and remains in the rumen for a long period of time without being regurgitated or otherwise eliminated from the rumen.

OBJECTS OF THE INVENTION

It is a principle object of this invention to provide both a novel and useful therapeutic dispensing device for the use in animal therapy that fulfills the pressing need known to the prior art.

Another object of the invention is to provide a therapeutic dispensing device that delivers a medicine or a nutrient at a controlled rate over a prolonged period of time.

Another object of the invention is to provide a therapeutic dispensing device that can remain in the rumen of a ruminant for a prolonged period of time.

Another object of the invention is to provide a therapeutic dispensing device that is self-contained, self-starting and self-powered in a fluid environment, is easy to make, and can be used for dispensing beneficial agents to a warm-blooded animal including a ruminant.

Another object of the invention is to provide a dispensing device comprising a wall surrounding an internal lumen containing a temperature sensitive beneficial agent composition and an expandable member containing a density producing member.

Another object of the invention is to provide a dispensing device comprising an internal space formed by a capsule arrangement that is easy to manufacture at low cost thereby increasing the usefulness and making the dispensing device practical for treating domestic animals.

Another object of the invention is to provide a dispensing device comprising a wall surrounding a capsule containing a temperature-sensitive beneficial agent composition, an expandable member comprising a hydrogel and a density increasing member, and a passageway useful for dispensing a beneficial agent to an animal.

Another object of the invention is to provide a dispensing device comprising a wall that surrounds an internal lumen, and which dispensing device delivers a thermo-sensitive composition containing a beneficial agent by the combined physical-chemical operations of the composition melting and becoming fluid to semi-solid or the like, with the composition being displaced from the device by an expanding member containing a density increasing member that swells and occupies space in the area initially occupied by the composition.

Another object of the invention is to provide a dispensing device comprising a dense member dispersed throughout an expandable member, for keeping the dispensing device in the rumen over time, and wherein the dispensing device administers a composition that is a complete pharmaceutical dosage regimen for a medical or nutritional effect over a prolonged period of time, the use of which dispensing device requires intervention only for the initiation of the regimen.

Another object of the invention is to provide a dispensing device that can deliver a beneficial drug contained in a thermo-responsive, lipophilic pharmaceutically acceptable carrier that melts in the rumen in the presence of thermal energy absorbed from environment of the rumen into a dispensable composition that is innocuous, thereby substantially avoiding mammalian tissue irritation and interaction with mammalian protein tissues.

Another object of the invention is to provide a dispensing device containing an eutectic composition formed of at least two components and at least one drug, which eutectic composition has a melting point approximately the same as the temperature of a warm-blooded animal's rumen, and is dispensed from the dispensing device at the temperature of the animal.

Another object of the invention is to provide a dispensing device comprising a dense member dispersed throughout an expandable member wherein, after the delivery period of the pharmaceutical composition, the expandable member is delivered causing a reduction in the density member thereby allowing the device to be passed from the environment of use.

Another object of the invention is to provide a dispensing device comprising an inner capsule housing a thermo-responsive hydrophobic composition comprising insoluble to soluble drugs, and which thermo-responsive composition in response to energy input present in the gastrointestinal tract of a ruminant, changes its form and becomes dispensable for operative delivery from the dispensing device.

Another object of the invention is to provide a dispensing device for dispensing a drug to a ruminant, which dispensing device comprises a walled body containing a thermoplastic composition that includes a beneficial agent that is poorly soluble in an aqueous environment and can be housed in the device in a nonaqueous dispensing carrier for delivery by an expandable component containing a density member to a ruminant.

Other objects, features and advantages of the invention will be more apparent to those skilled in the dispensing art form the following detailed description of the specification, taken in conjunction with the drawings and the accompanying claims.

BRIEF DESCRIPTION OF THE DRAWINGS

In the drawing figures, which are not drawn to scale, but are set forth to illustrate various embodiments of the invention, the drawing figures are as follows.

In the drawing figures and in the specifications, like parts in related drawing figures are identified by like parts. The terms appearing earlier in the specification and in the description of the drawing figures as well as embodiments thereof, are further detailed elsewhere in the disclosure.

DETAILED DESCRIPTION OF THE DRAWINGS

Figure 1:
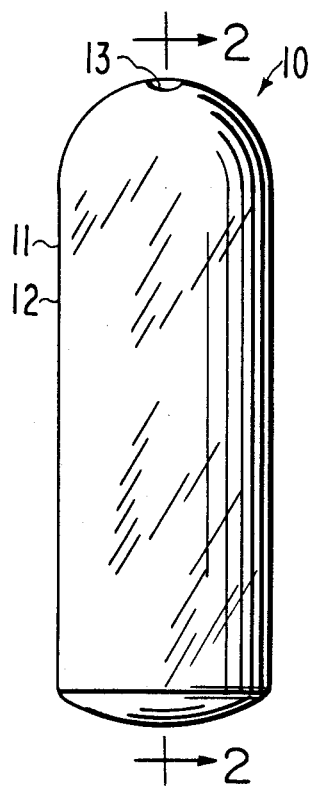
FIG. 1 is a view of a dispensing device designed and manufactured for orally administering a beneficial agent to a warm-blooded ruminant animal.

Turning now to the drawing figures in detail, which are examples of the novel and useful dispensing device of the invention, which examples are not to be construed as limiting, one example of a therapeutic dispensing device is seen in FIG. 1, identified by the numeral 10. In FIG. 1, dispensing device 10 comprises a body 11 formed of a wall that surrounds and forms an internal lumen, not seen in FIG. 1. Therapeutic dispensing device 10 comprises at least one passageway 13 preformed or formed during use in wall 12 for delivering a beneficial agent from dispensing device 10.

Figure 2:
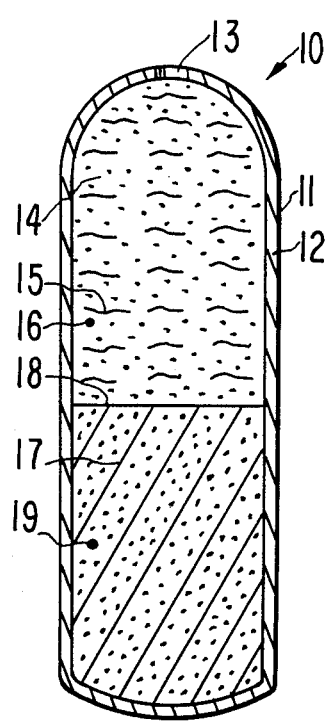
FIG. 2 is an opened view of the dispensing device of FIG. 1 as seen through 2—2 the vertical length of the dispensing device for depicting the structure of the dispensing device comprising a wall, a thermo-responsive composition and an expandable member containing a density member.

FIG. 2 is an opened, sectional view of dispensing device 10 of FIG. 1. Therapeutic dispensing device 10 of FIG. 2 comprises body 11, wall 12 and passageway 13. Wall 12 surrounds and defines an internal compartment 14, an internal lumen. In a presently preferred embodiment wall 12 is formed in at least a part, or totally, of a semipermeable wall-forming composition. The semipermeable composition is substantially permeable to the passage of an external fluid, and it is substantially impermeable to the passage of a beneficial agent and other ingredients contained in dispensing device 10. When wall 12 is formed in at least a part of a semipermeable composition, the rest of wall 12 is formed of a wall-forming composition that is substantially impermeable to the passage of fluid and substantially impermeable to the passage of a beneficial agent and other ingredients housed in device 10. Wall 12 is non-toxic, and it maintains its physical and chemical integrity. That is, it is inert, and it does not erode during the dispensing period. Lumen 14 contains a thermo-responsive heat sensitive composition 15, identified by wavy lines, containing a beneficial agent 16, represented by dots. Lumen 14 further contains an expandable driving member 17 that is in one embodiment in layer contact with at contacting surfaces 18 with thermo-responsive composition 15. Expandable driving member 17 contains a density member 19, identified by dots, dispersed therein. Density member 19, a densifier, is a component of dispensing device 10 for keeping device 10 in the rumen of an animal during the beneficial agent dispensing period. Thermo-responsive composition 15 and driving member 17 possess a shape that corresponds to the internal shape of lumen 14. A passageway 13 extends through semipermeable wall 12 for communicating lumen 14 and the exterior of device 10.

Figure 3:
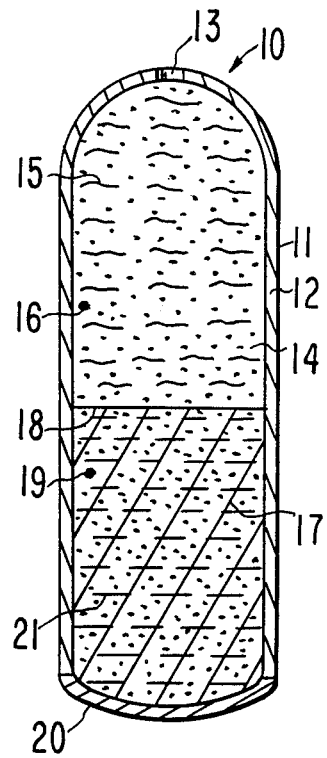
FIG. 3 is an opened view of the dispensing device of FIG. 1 as seen through 2—2 thereof, with FIG. 3 depicting another embodiment of the invention wherein the expandable member contains both a density member and an osmotic solute.

FIG. 3 depicts another manufacture provided by the invention. FIG. 3 is an opened view of dispensing device of FIG. 1, and it comprises body 11, wall 12, passageway 13, and internal compartment 14. Wall 12 in FIG. 3 is formed of a wall-forming composition that is impermeable to both fluid and agents, except for a part of wall 12 at wall 20 that is formed of a wall-forming material that is permeable to fluid and impermeable to agents. In FIG. 3, compartment 14 contains thermo-responsive composition 15 comprising beneficial agent 16 in laminar arrangement with driving member 17 containing weight means 19. In FIG. 3, driving member 17 contains an osmotically effective solute 21 that exhibits an osmotic pressure gradient across semipermeable wall 20 against an external fluid present in the environment of use. In operation, driving member 17 imbibes and absorbs fluid and osmotic solute 21 imbibes fluid, which combined operation causes driving member to expand and urge thermo-responsive composition 15 through passageway 13 to the environment of use.

Figure 4:
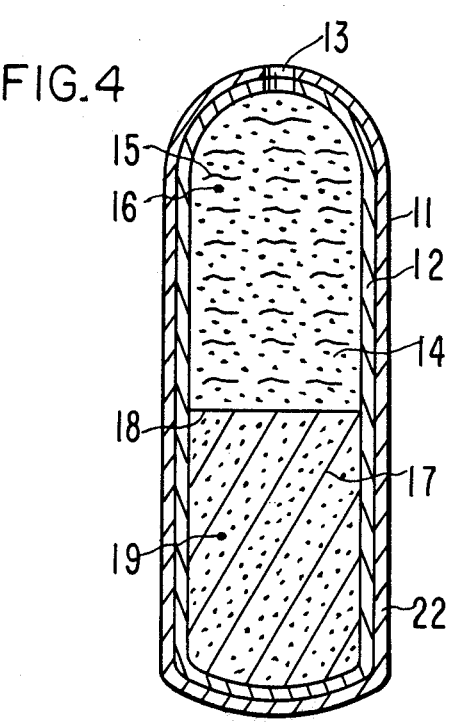
FIG. 4 is an opened view of the dispensing device of the invention comprising an inner and an outer wall presently formed of different wall forming materials; and, FIG. 5 is an opened view of the dispensing device of the invention illustrating the device near the end of a delivery period.

FIG. 4 is an opened view of another dispensing device 10 provided by the invention. Dispensing device 10 of FIG. 4 is similar to device 10 of FIGS. 1 through 3, with the added embodiment that FIG. 4, wall 12 is an internal capsule which surrounds compartment 14. Wall 12 comprising the internal capsule is surrounded by an outer semipermeable wall 22 that is permeable to the passage of fluid and impermeable to the passage of an agent. The internal capsule used for forming inner wall 12 can comprise a single unit capsule body member, or it can be a dual capsule body member, not seen in FIG. 4. Passageway 13 extends through outer semipermeable wall 22 and inner wall 12 for delivering the thermo-responsive beneficial agent composition to the exterior of device 10.

Figure 5:
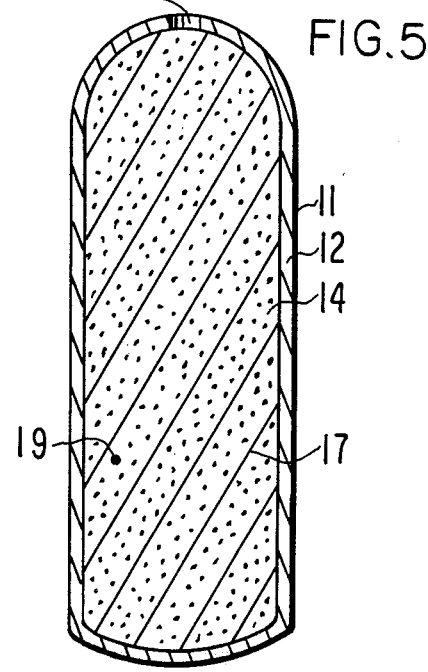

Therapeutic dispensing device 10 of FIGS. 1 through 4, in operation in a fluid biological environment of use, delivers beneficial agent 16 by a combination of thermodynamic and kinetic integrally performed activities. That is, in operation heat sensitive composition 15, in response to the temperature of the rumen, absorbs thermal energy, melts and forms a deliverable composition, for example, a fluidic, a semi-paste or like deliverable composition for dispensing beneficial agent 16 through passageway 13. As composition 15 softens, melts or becomes flowable, external fluid is concomitantly imbibed through semipermeable wall 12 by expandable hydrophilic composition 17. Expandable composition 17 imbibes fluid in a tendency towards osmotic equilibrium causing it to continuously expand or swell. As layer 17 expands and swells, it increases in size and volume simultaneously moving against composition 15 thereby urging composition 15 through passageway 13. In a presently preferred embodiment layer 17 expands while maintaining an intact immiscible boundary at interface 18 defined by heat sensitive composition 15 and expandable layer 17. In the embodiment wherein expandable layer 17 contains an osmotically effective solute 21, solute 21 imbibes fluid through the semipermeable wall into dispenser 10. This fluid serves two purposes, it becomes available for expandable hydrogel 17 for it to swell to a maximum dimension, and it increases the fluidic volume in the area of expandable hydrogel 17 for it to apply pressure against composition 15 Device 10 is maintained in the rumen by the presence of dense member 19 contained in expandable member 17 throughout the dispensing operation of device 10. Initially the density or mass per unit volume of device 10 is such that device 10 remains in the rumen. As beneficial composition 15 is dispensed from device 10, density is maintained by imbibition of water into expandable member 17 balancing delivery of beneficial composition, and as expandable member 17 occupies compartment 14 and is dispensed fully through passageway 13, as seen in FIG. 5, the density of device 10 drops so that it will pass with the ruminal contents. In this operation, device 10 goes from a rumen-retentive to a rumenexpellable device over time.

The dispensing device 10 can be manufactured in a variety of sizes and shapes for administering device 10 to ruminant animals. One presently preferred shape is a cylinder-like or capsule-like shape. For example, for use with sheep, delivery system 10 can embrace a capsule-like shape and have a diameter of about 0.5 inches to 1 inch (1.3 cm to 2.5 cm) and a length of about 0.5 inches to 2.5 inches (1.3 cm to 6.6 cm). For use with cattle, system 10 has a diameter of about 0.5 inches to 1.5 inches (1.3 cm to 3.8 cm), and a length of about 1 inch to 3.5 inches (2.5 cm to 7.8 cm). While FIGS. 1 through 5 illustrate various delivery systems 10 that can be made according to the invention, it is to be understood these systems are not to be construed as limiting the invention, as the dispenser can take other shapes, sizes and forms for delivering beneficial agents to the biological environment of use. The delivery system can be used in medical devices, hospitals, veterinary clinics, farms, zoos, laboratories, physician's offices, on the range, in feed lots, and other environments of use.

DETAILED DESCRIPTION OF THE INVENTION

In accordance with the practice of this invention, it has now been found representative materials for forming a wall include semipermeable homopolymers, semipermeable copolymers, and the like. In one embodiment typical materials include cellulose esters, cellulose monoesters, cellulose diesters, cellulose triesters, cellulose ethers, and cellulose ester-ethers, mixtures thereof, and the like. These cellulosic polymers have a degree of substitution, D.S., on their anhydroglucose unit from greater than 0 up to 3 inclusive. By degree of substitution is meant the average number of hydroxyl groups originally present on the anhydroglucose unit that are replaced by a substituting group, or converted into another group. The anhydroglucose unit can be partially or completely substituted with groups such as acyl, alkanoyl, aroyl, alkyl, alkenyl, alkoxy, halogen, carboalkyl, alkylcarbamate, alkylcarbonate, alkylsulfonate, alkylsufamate, and like semipermeable polymer forming groups. The semipermeable materials typically include a member selected from the group consisting of cellulose acylate, cellulose diacylate, cellulose triacylate, cellulose acetate, cellulose diacetate, cellulose triacetate, nono-, di- and tri-cellulose alkanylates, mono-, di- and tri-alkenylates, mono-, di- and tri-aroylates, and the like. exemplary polymers including cellulose acetate having a D.S. of 1.8 to 2.3 and an acetyl content of 32 to 39.9%., cellulose diacetate having a D.S. of 1 to 2 and an acetyl content of 21 to 35%; cellulose triacetate having a D.S. of 2 to 3 and an acetyl content of 34 to 44.8% and the like. More specific cellulosic polymers include cellulose propionate having a D.S. of 1.8 and a propionyl content of 38.5%; cellulose acetate propionate having an acetyl content of 1.5 to 7% and an acetyl content of 39 to 42%; cellulose acetate propionate having an acetyl content of 2.5 to 3%, an average propionyl content of 39.2 to 45% and a hydroxyl content of 2.8 to 5.4%; cellulose acetate butyrate having a D.S. of 1.8, and acetyl content of 13 to 15%, and a butyryl content of 34 to 29%; cellulose acetate butyrate having an acetyl content of 2 to 29.5%, a butyryl content of 7 to 52%, and a hydroxyl content of 0.5 to 4.7%; cellulose triacylates having a D.S. of 2.9 to 3 such as cellulose trivalerate, cellulose trilaurate, cellulose tripalmitate, cellulose trioctanoate, and cellulose tripropionate; cellulose diesters having a D.S. of 2.2 to 2.6 such as cellulose disuccinate, cellulose dipalmitate, cellulose dioctanoate, cellulose dicarpylate; cellulose propionate morpholinobutyrate; cellulose acetate butyrate; cellulose acetate phthalate, and the like; mixed cellulose esters such as cellulose acetate valerate, cellulose acetate succinate, cellulose propionate succinate, cellulose acetate octanoate, cellulose valerate palmitate, cellulose acetate heptonate, and the like. Semipermeable polymer are known in U.S. Pat.

No. 4,077,407, and they can be made by procedures described in *Encyclopedia of Polymer Science and Technology* Vol. 3, pp 325 to 354, 1964, published by Interscience Publishers, Inc., New York.

Additional semipermeable polymers includes cellulose acetaldehyde dimethyl cellulose acetate., cellulose acetate ethylcarbamate; cellulose acetate methylcarbamate; cellulose dimethylaminoacetate; a cellulose composition comprising cellulose acetate and hydroxypropyl methylcellulose; a composition comprising cellulose acetate and cellulose acetate butyrate; a cellulose composition comprising cellulose acetate butyrate and hydroxypropyl methylcellulose; semi-permeable polyamides; semipermeable polyurethanes; semipermeable polyamides; semipermeable polyurethanes; semipermeable polysulfane; semipermeable sulfonated polystyrenes, cross-linked, selectively semipermeable polymers formed by the coprecipitation of a polyanion and a polycation as disclosed in U.S. Pat. Nos. 3,173,876; 3,276,586; 3,541,005; 3,541,006 and 3,546,142; selectively semi-permeable silicon rubbers; semipermeable polymer as disclosed by Loeb and Sourirajan in U.S. Pat. No. 3,133,132; semi-permeable polystyrene derivatives; semipermeable (polysodium-styrenesulfonate); semipermeable poly(vinylbenzyltrimethyl) ammonium chloride; semipermeable polymer exhibiting a fluid permeability of $10^{-1}$ to $10^{-7}$ (cc.mil/cm$^2$ hr.atm) expressed as per atmosphere of hydrostatic or osmotic pressure difference across a semipermeable wall. The polymers are known to the art in U.S. Pat. Nos. 3,845,770; 3,916,899 and 4,160,020, and in *Handbook of Common Polymers* by J. R. Scott and W. J. Roff, 1971, published by CRC Press, Cleveland, OH.

In the manufacture wherein device 10 comprises a capsule member, the capsule member generally is tubular shaped and it has a mouth at one end, and at the end distant therefrom it is closed in a hemi-spherical or dome shaped end. The capsule member serves as a hollow body having a wall that surrounds and defines an interior compartment provided with an opening for establishing communication with the exterior of the capsule and for filling the capsule. In one embodiment, a capsule is made by dipping a mandrel, such as a stainless steel mandrel, into a bath containing a solution of a capsule wall forming material to coat the mandrel with the material. Then, the mandrel is withdrawn, cooled and dried in a current of air. The capsule is stripped from the mandrel and trimmed to yield a capsule with an internal lumen. The materials used for forming the capsule are then commercially available materials including gelatin, gelatin having a viscosity of 15 to 30 millipoises and a bloom strength up to 150 grams; gelatin having a bloom value of 160 to 250; a composition comprising gelatin, glycerine water and titanium dioxide; a composition comprising gelatin, erythrosin, iron oxide and titanium dioxide; a composition comprising gelatin, glycerine, sorbitol, potassium sorbate and titanium dioxide; a composition comprising gelatin, acacia, glycerin and water; water soluble polymers that permit the transport of water therethrough and can be made into capsules, and the like.

The wall of device 10 also can comprise a flux regulating agent. The flux regulating agent is a compound added to a wall forming composition that assists in regulating the fluid permeability of flux through the wall. The flux regulating agent can be a flux enhancing agent or a flux decreasing agent. The agent can be preselected to increase or decrease the liquid flux. Agents that produce a marked increase in permeability to fluid such as water, are often essential hydrophilic, while those that produce a marked decrease to fluids such as water, are essentially hydrophobic. The amount of regulator in the wall when incorporated therein generally is from about 0.01% to 20% by weight or more. The flux regulator agents in one embodiment that increase flux include polyhydric alcohols, polyalkylene glycols, polyalkylenediols, polyesters of alkylene glycols and the like. Typical flux enhancers include polyethylene glycol 300, 400, 600, 1000, 4000, 6000 and the like; low molecular weight glycols such as polypropylene glycol, polybutylene glycol and polyamylene glycol; the polyalkylenediols such as poly(1,3-propanediol), poly(1,4-butanediol), poly(1,6-hexanediol) and the like; aliphatic diols such as 1,3-butylene glycol, 1,4-pentamethylene glycol, 1,4-hexamethylene glycol, and the like; alkylene triols such as glycerine, 1,2,3-butanetriol, 1,2,4-hexanetriol, 1,3,6-hexanetriol and the like; ester such as ethylene glycol dipropionate, ethylene glycol butyrate, butylene glycol dipropionate glycerol acetate esters, and the like. Representative flux decreasing agents include phthalates substituted with an alkyl, an alkoxy or with both an alkyl and alkoxy group such as diethyl phthalate, dimethoxyethyl phthalate, dimethyl phthalate, and [di(2-ethyl-hexyl)phthalate]; aryl phthalate such as triphenyl phthalate, and butyl benzyl phthalate; insoluble salts such as calcium.sulphate, barium sulphate, calcium phosphate, and the like; insoluble oxides such as titanium oxide; polymers in powder, granule and like form such as polystyrene, polymethylmethacrylate, poly-carbonate, and polysulfone; esters such as citric acid esters esterified with long chain alkyl groups; inert and substantially water impermeable fillers; resins compatible with cellulose based wall forming materials, and the like.

Other materials that can be used to impart flexibility and elongation properties to the wall, for making the wall less-to-nonbrittle, and for increasing tear strength include plasticizers, presently exemplified by phthalate plasticizers such as dibenzyl phthalate, dihexyl phthalate, butyl octyl phthalate, straight chain phthalates of six to eleven carbons, diisononyl phthalate, diisodecyl phthalate, and the like. The plasticizers include nonphthalates such as citric acid esters, triacetin, dioctyl azelate, epoxidized tallate, triisoctyl trimellitate, triisononyl trimellitate, sucrose acetate isobutyrate, epoxidized soybean oil and the like. The plasticizers include nonphthalates such as triacetin, dioctyl azelate, epoxidized tallate, triisoctyl trimellitate, triisononyl trimellitate, sucrose acetate isobutyrate, epoxidized soybean oil, and the like. The amount of plasticizer in a wall when incorporated therein is about 0.01% to 20% by weight, or higher.

Expandable means 17 preferably has a shape that corresponds to the internal shape of compartment 14 and it is made from a hydrogel composition. The hydrogel composition is noncross-linked or optionally cross-linked and it possesses properties, such as the ability to absorb and/or imbibe an exterior fluid through the wall, and when it is an osmotic-acting hydrogel it exhibits an osmotic pressure gradient across the wall against a fluid outside delivery system 10. The materials used for forming the swellable, expandable inner layer 17 are polymeric materials neat, and polymeric materials blended with osmotic agents that interact with water or a biological fluid, absorb the fluid and swell or expand to an equilibrium state. The polymer exhibits the ability to retain a significant fraction of imbibed fluid in the polymer molecular structure. The polymers in a preferred embodiment are gel polymers that can swell or expand to a very high degree, usually exhibiting a 2 to 50 fold volume increase. The swellable, hydrophilic polymers that function by osmotic properties, also known as osmopolymers which osmopolymers can be noncross-linked or lightly cross-linked. The cross-links can be covalent or ionic bonds with the polymer possessing the ability to swell in the presence of fluid, and when cross-linked it will not dissolve in the presence of aqueous fluid. The polymer can be of plant, animal or synthetic origin. Polymeric materials useful for the present purpose include poly(hydroxyalkyl methacrylate) having a molecular weight of from 5,000 to 5,000,000; poly(-vinylpyrrolidone) having a molecular weight of from 10,000 to 360,000; anionic and cationic expandable hydrogels; poly(electrolyte) complexes; poly(vinyl alcohol) having a low acetate residual; a swellable mixture of agar and carboxymethyl cellulose; a swellable composition comprising methyl cellulose mixed with a sparingly cross-linked agar; a water-swellable copolymer reduced by a dispersion of finely divided copolymer of maleic anhydride with styrene, ethylene, propylene, or isobutylene; water swellable polymer of N-vinyl lactams; and the like.

Other hydrogel or gelable fluid absorbing or imbibing and retaining polymers useful for forming hydrophilic, expandable push member 17 include pectin having a molecular weight ranging from 30,000 to 300,000; polysaccharides such as agar, acacia, karaya, tragacanth, algins and guar; Carbopol ® acidic carboxy polymer and its salt derivatives; polyacrylamides; water-swellable indene maleic anhydride polymers; Good-rite ® polyacrylic acid having a molecular weight of 80,000 to 200,000; Polyox ® polyethylene oxide polymers having a molecular weight of 100,000 to 5,000,000; starch graft copolymers; Aqua-Keep ® acrylate polymers with water absorbability of about 400 times its original weight; diesters of polyglucan; a mixture of cross-linked polyvinyl alcohol and poly(N-vinyl-2-pyrrolidone); zein available as prolamine; poly(ethylene glycol) having a molecular weight of 4,000 to 100,000; and the like. In a preferred embodiment, the expandable member is formed from polymer and polymeric compositions that are thermoformable. Representative polymers possessing hydrophilic properties are known in U.S. Pat. Nos. 3,865,108; 4,022,173; 4,207,893, 4,327,725, and in *Handbook of Common Polymers,* by Scott and Roff, published by Cleveland Rubber Company, Cleveland, OH.

The osmotically effective compound that can be blended homogeneously or heterogeneously with the swellable polymer means 17, to form push member 17, are the osmotically effective solutes that are soluble in fluid imbibed into the swellable polymer, and exhibit an osmotic pressure gradient across the semipermeable wall against an exterior fluid. Osmotically effective compounds are known in the dispensing art also as osmagents. Osmotically effective osmagents useful for the present purpose include magnesium sulfate, magnesium chloride, sodium chloride, lithium chloride, potassium sulfate, sodium sulfate, mannitol, urea, sorbitol, inositol, succrose, glucose, and the like. The osmotic pressure in atmospheres, atm, of the osmagents suitable for the invention will be greater than zero atm, generally from eight atm up to 500 atm, or higher. The swellable, expandable polymer, in addition to providing a driving source for delivering a beneficial agent formulation 15 from the dispenser 10, further serves to function as a supporting matrix for an osmotically effective solute. The composition in a presently preferred embodiment comprises at least one expandable polymer and at least one osmotic solute. Generally an expandable composition will comprise about 20% to 90% by weight of polymer and 80% to 10% by weight of osmotic solute, with a presently preferred expandable composition comprising 35% to 75% by weight of expandable polymer and 65% to 25% by weight of osmotic solute.

The weight means, or density increasing member, also referred to as densifier, that is homogeneously or heterogeneously dispersed throughout the expandable hydrogel is used for initially retaining device 10 in the rumen-reticular sac of a ruminant. The dense member lets device 10 remain in the rumen during the dispensing period before device 10 passes into the alimentary tract and is eliminated therefrom. During the period of time device 10 remains in the rumen, beneficial active agent is delivered by device 10 at a controlled rate to the ruminant over time. Generally the amount of weight means mixed with the expandable hydrogel will be an amount sufficient to impart an initial density to the expanding hydrogel of greater than 1 to 8, with the density in a presently preferred embodiment exhibiting a specific gravity of from 2.2 to 7.6. For ruminant cattle and sheep it is presently preferred the combination expandable hydrogel weight means initially exhibit a density such that there is a resulting system density of about 3. Materials that have a density of from 1 to 8 that can be blended with the hydrogel include iron, iron shot, iron shot coated with iron oxide, iron shot magnesium alloy, steel, stainless steel, copper oxide, a mixture of cobalt oxide and iron powder, a mixture of iron and copper oxide, and the like. The weight means can be in powder, granule, pellet and like form for blending with the hydrogel. The weight means can be blended with the hydrogel during polymerization, by blending solvent casting and evaporating, by compressing a blend and the like. The amount of weight means blended with a hydrogel is about 0.5 to 50 volume percent, or an amount sufficient volume determinations are easily performed by procedures known in the art s disclosed in *Remington's Pharmaceutical Sciences,* Vol. 14, pp 95 to 100, edited by Osol, 1970, by Mack Publishing Co., Easton, Pa.

The thermo-responsive composition containing a beneficial agent homogeneously or heterogeneously dispersed or dissolved therein, is formed in a presently preferred embodiment of a heat sensitive, hydrophilic or hydrophobic material that exhibits solid-like properties at room temperature of 24° C., and within a few centigrade degrees thereof, and exhibits in a preferred embodiment a melting point of 24° C. to 45° C. that, in a preferred embodiment, approximates mammalian body temperatures of 37° C. and within a few centigrade degrees thereof. The present invention uses the phrases "melting point", "softening point", "pour point", or "liquifies" to indicate the temperature at which the thermo-responsive composition melts, undergoes dissolution, or forms a paste-like ribbon, dissolves to form a dispensable carrier so it can be used for dispensing the beneficial agent from dispenser 10. The term "thermo-responsive" as used for the purpose of this invention includes thermoplastic compositions capable of softening, melting, becoming extrudable, becoming fluid, or becoming dispensable in response to heat and hardening again when cooled. The term also includes thermo-tropic compositions capable of undergoing change and becoming dispensable in response to the application of energy in a gradient manner. These materials also are temperature sensitive in their response to the application, and to the withdrawal of energy. The term "thermo-responsive" as used for the purpose of this invention in a preferred embodiment denotes the physical-chemical property of a composition agent carrier to exhibit storage or solid, or solid-like properties at temperatures up to 24° C., and become fluid, semisolid, or viscous when disturbed by heat at, usually in the range of 24° C. to 45° C. The thermo-responsive carrier is heat-sensitive and preferably anhydrous and it has the property of melting, dissolving, undergoing dissolution, softening, or liquifying at the elevated temperatures, thereby making it possible for the dispenser 10 to deliver the thermo-responsive carrier with the beneficial agent homogeneously or heterogeneously blended therein. The thermo-responsive carrier can be lipophilic, hydrophilic or hydrophobic. Another important property of the carrier is its ability to maintain the stability of the agent contained therein during storage and during delivery of the agent. Representative thermoresponsive compositions and their melting points are as follows: cocoa butter, 32° to 34° C.; cocoa butter plus 2% beeswax, 35° to 37° C.; propylene glycol monostearate and distearate, 32° to 35° C.; hydrogenated oils such as hydrogenated vegetable oil, 36° to 37.5° C.; 80% hydrogenated vegetable oil and 20% sorbitan monopalmitate, 39° to 39.5° C.; 80% hydrogenated vegetable oil and 20% polysorbate 60, 36° to 37° C.; 77.5% hydrogenated vegetable oil with 20% sorbitan trioleate and 2.5% beeswax, 35° to 36° C.; 72.5% hydrogenated vegetable oil with 20% sorbitan trioleate, 2.5% beeswax and 5.0% distilled water, 37° to 38° C.; mono-, di-, and triglycerides of acids having from 8–22 carbon atoms including saturated and unsaturated acids such as palmitic, stearic, oleic, lineolic, linolenic and archidonic., glycerides of fatty acids having a melting point of at least 32° C. such as monoglycerides, diglycerides and triglycerides of vegetable fatty acids having 10 to 18 carbon atoms obtained from coconut oil, olive oil and the like; partially hydrogenated cottonseed oil, 35° to 39° C.; hardened fatty alcohols and fats, 33° to 36° C.; hexadienol and hydrous lanolin triethanolamine glyceryl monostearate, 38° C.; eutectic mixtures of mono-, di-, and triglycerides, 35° to 39° C.; Witepsol® #15, triglyceride of saturated vegetable fatty acid with monoglycerides, 33.5° to 35.5° C., Witepsol® H32 free of hydroxyl groups, 31° to 33° C.; Witepsol® W2 having a saponification value of 225-240 and a melting point of 33.5° to 35.5° C.; Witepsol® #75 having a saponification value of 220-230 and a melting point of 37° to 39° C., a polyalkylene glycol such as polyethylene glycol 1000, a linear polymer of ethylene oxide, 38° to 41° C.; polyethylene glycol 1500, melting at 38° to 41° C.; polyethylene glycol monostearate, 39° to 42.5° C.; 33% polyethylene glycol 1500, 47% polyethylene glycol 6000 and 20% distilled water, 39° to 41° C.; 30% polyethylene glycol 1500, 40% polyethylene glycol 4000 and 30% polyethlene glycol 400, 33° to 38° C.; mixture of mono-, di-, and triglycerides of saturated fatty acids having 11 to 17 carbon atoms, 33° to 35° C.; block polymer of 1,2-butylene oxide and ethylene oxide; block polymer of propylene oxide and ethylene oxide; block polymer of polyoxyalkylene and propylene glycol, and the like. The thermo-responsive composition is a means for storing a beneficial agent in a solid composition at a temperature up to 24° C., maintaining an immiscible boundary at the swelling composition interface, and for dispensing the agent in a flowable composition at a temperature greater than 24° C., and preferably in the range of 24° C. to 45° C. The thermo-responsive composition on being dispensed into a biological environment are easily excreted, metabolized, assimilated, or the like, for effective use of the beneficial agent.

The term "beneficial agent" as used herein includes medicines or drugs, nutrients, vitamines, anthelminthic, biocide, larvicides, fluikicides, parasiticide, anti-infection agents, antibloat agents, food supplements including mineral supplements, growth promotants and permittants, growth efficiency factors, chemical markers, and other agents that benefit a ruminant animal. The beneficial agent can be insoluble to very soluble in the temperature sensitive material housed in the delivery system. The amount of agent present in a delivery system can be from 10 ng to 40 g or more. The delivery system can house various amounts of the beneficial agent, for example, 75 ng, 1 mg, 5 mg, 100 mg, 250 mg, 750 mg, 1.5 mg, 2 g, 5 g, 10 g, 15 g, and the like. A single delivery system can be administered to a ruminant, or more than one delivery system can be administered to a ruminant during a therapeutic program. A delivery system can deliver from 0.1 mg/hr to 1500 mg/hr, or more, over a prolonged period of time. The delivery system can be used for one day to six months or longer.

Representative of beneficial agent that can be dispensed using the delivery system of this invention include anthelminthics such as mebendabzole, levamisole, albendazole, cambendazole, fenbendazole, parbendazole, oxfendazole, oxybendazole, thiabendazole, tichlorfon, praziquantel, morantel and pyrantel, and the like. Antiparasitic agents such as avermectins and ivermectin, as disclosed in U.S. Pat. Nos. 4,199,569 and 4,389,397, both assigned to Merck and Co., and in *Science*, Vol. 221, pp 823-828, 1983, wherein said ivermectin antiparasitic drug is disclosed as useful for aiding in controlling commonly occurring infestations in animals, such as roundworms, lungworms, and the like, and said ivermectin also being useful for management of insect infestations such as grub, lice, mange mite, and the like., antimicrobial agents such as chlortetracycline, oxytetracycline, tetracycline, streptomycin, dihydrostreptomycin, bacitracins, erythromycin, ampicillins, penicillins, cephalosporins, and the like; sulfa drugs such as sulfamethazine, sulfathiazole, and the like; growth stimulants such as Monesin® sodium and Elfazepam®; defleaing agents such as dexamethazone and flumethazone; rumen fermentation manipulators and ionophores such as lasalocid, virginamycin and ronnel, salinomycin; minerals and mineral salts; anti-bloat agents such as organopoly siloxanes; hormone growth supplements such as stilbestrol; growth efficiency factors such as -agonists, clenbuterol; vitamins; antienteritis agents such as furazolidone; nutritional supplements such as lysine monohydrochloride, methionine, magnesium carbonate, and the like; chemical markers such as chromic oxide and salts of yitterbium and erbium.

The wall forming composition can be applied to form the device and as the exterior surface of the capsule in laminar arrangement by molding, air spraying, dipping, casting, or brushing, with a wall forming composition. Other and presently preferred techniques that can be used for applying the wall are the air suspension procedure and the pan coating procedure. The air procedure consists in suspending and tumbling the compress arrangement of the device forming components in a current of air and a wall forming composition until the wall surrounds and coats the components or surrounds and coats the capsule member. The procedure can be repeated with a different semipermeable wall forming composition to form a laminated wall. The air suspension procedure is described in U.S. Pat. No. 2,799,241; *J. Am. Pharm. Assoc.*, Vol. 48, pp 451–459, 1979; and ibid., Vol. 49, pp 82–84, 1960. Other standard manufacturing procedures are described in *Modern Plastics Encyclopedia*, Vol. 46, pp 62–70, 1969; in *Pharmaceutical Sciences*, by Remington 14th Ed., pp 1626–1678, 1970, published by Mack Publishing Co., Easton, Pa.

Exemplary solvent suitable for manufacturing the wall include inert inorganic and organic solvents that do not adversely harm the materials, the capsule wall, the beneficial agent, the thermo-responsive composition, the expandable member, the dense member, and the final dispenser. The solvents broadly include members selected from the group consisting of aqueous solvents, alcohols, ketones, esters, ethers, alphatic hydrocarbons, halogenated solvents, cycloaliphatics, aromatics, heterocyclic solvents and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyclo-octane, benzene, toluene, naptha, 1,4-dioxane, tetrahydrofuran, diglyme, water, and mixtures thereof such as acetone and water, acetone and methanol, acetone and ethyl alcohol, methylene dichloride and methanol, and ethylene dichloride and methanol. Generally for the present purpose the semipermeable wall is applied at a temperature a few degrees less then the melting point of the thermo-responsive composition. Or, the thermoplastic composition can be loaded into the dispenser after applying the semipermeable wall.

The expression "passageway" or "orifice" as used herein comprises means and methods in the wall or in a laminated wall suitable for releasing a beneficial agent formulation from the dispenser. The passageway can be formed by mechanical or laser drilling, or by eroding an erodible element in the wall, such as gelatin plug. The passageway can be drilled through the semipermeable wall only, or through the semipermeable wall capsule laminated wall. In these embodiments when the passageway is drilled only through the semipermeable wall, the passageway in the capsule wall is formed in the environment of use by bursting, eroding or dissolving a passageway in the capsule wall. The passageway can be a porous polymer composition having at least one pore, or a microporous polymer composition having at least one micropore or more than one micropores that serve as more than one passageway suitable made a part of the wall of the delivery system. The microporous releasing means can be formed by learching a pore former from the wall. The passageway can be positioned in a preselected loci of the wall by visual inspection, by optical density scanning as the device travels through a laser machine, by orienting and following the device through the manufacturing steps, by photo detection and responding to the reflected wave length emanating from a device, by magnetic orientation, and like standard manufacturing procedures. A detailed description of some orifice and the preferred maximum and minimum dimensions for an orifice are disclosed in U.S. Pat. Nos. 3,845,770 and 3,916,899.

DESCRIPTION OF EXAMPLES OF THE INVENTION

The following examples are merely illustrative of the present invention and they should not be construed as limiting the scope of the invention in any way, as these examples and other equivalents thereof will become more apparent to those skilled in the art in the light of the present disclosure, the drawings and the accompanying claims.

EXAMPLE 1

A dispensing system for the controlled delivery of ivermectin is made as follows: first, 193 g of Butronic ® L-1 polyol, a block polymer formed by the polymerization of 1,2-butylene oxide to which ethylene oxide is added, as reported in *Cosmetics and Toiletries*, Vol. 97, pp 61–66, 1982, which polymer flows at a pour point of 39° C., is melted at 55° C. and then 13.98 g of ivermectin is added thereto using a high sheer ultrasonic mixer. The resulting mixture is placed in a vacuum oven at 55° C. and the pressure reduced to less than 10 mm of mercury. The ivermectin Butronic ® composition is allowed to remain in the vacuum for a period of about 10 minutes for removing entrapped air. Next, 4 g of the resulting thermoplastic drug formulation is poured through the open tail end into the lead end of a ½ oz. gelatin capsule. Then, an expandable driving member comprising 1.2 g of sodium chloride, 4.6 g of the sodium salt of polyacrylic acid available as Carbopol ® 934-P and 30 g or iron chip are compressed into a solid mass shaped like a tablet. The tablet is formed using a 18.2 mm tableting tool and a 3½ ton compression force and has a final shape that corresponds to the internal shape of the opening of the capsule. The tablet member is inserted into the opened end of the capsule until contact is made with the drug polyol formation. Next, the capsule is coated in a pan coater with a rate controlling wall comprising 1.8 g of 91% cellulose acetate butyrate and 9% polyethylene glycol 400. The wall is coated from a 5% wt/wt solution in methylene chloride methanol 90:10 v/v solvent system. The wall coated delivery systems then are dried at 30° C. for 24 hours. Next, the device is visually oriented and a 30 mil exit passageway is drilled through the semipermeable wall and the gelatin capsule using a high speed mechanical drill for communicating the passageway with the internal compartment of the device. The passageway establishes communication with the heat-responsive drug formulation for delivering it from the delivery system. The dispenser made according to this example has an average release rate of 0.5 mg per hour over a 480 hour period of time.

EXAMPLE 2

A delivery system is made according to the procedure set forth in Example 1, with the conditions as set forth, except that in this example the heat-responsive composition comprises 46.6 g of ivermectin and 200 g of polyethylene glycol 400 distearate, and the expandable-swellable composition comprises 70% by weight of poly(ethylene oxide) having a molecular weight of 3,000,000, 10% by weight of sodium chloride, and 20% by weight of a 50:50 mixture of iron shot and cobalt oxide. Delivery systems prepared according to this example dispense from 0.100 to 0.750 mg/hr of the ivermectin.

EXAMPLE 3

A dispenser system is prepared as follows: first, the body section of a capsule is positioned with its mouth in an upright position, and a layer of an expandable-swellable density composition is charged into the hemispherical end of the capsule. The layer's shape matches the internal shape of the capsule. The composition comprises 5% by weight of sodium chloride, 70% by weight of poly(ethylene oxide) having a molecular weight of 200,000 and 25% by weight of stainless steel tiny particles. The expandable-swellable density composition forming ingredients are blended in a commercial blender with heat for 20 minutes to yield a homogeneous composition. The heated composition is charged into the capsule forming a layer that occupies about ⅓ of the capsule. Next, a heat-sensitive drug formulation comprising an eutectic mixture of 77% neutral fat having a melting point of 35°–37° C. and 19.5% paraffin having a melting point of 52° C. is heated and 3.5% levamisole is added thereto. Then, the heated mixture is cooled to about 40° C. and injected into the capsule in contacting relation with the expandable layer, and the capsule allowed to cool to room temperature.

Then a solution of cellulose acetate, 15 wt percent, with an acetyl content of 39.8%, is prepared in a methylene chloride methanol solvent system and the capsule coated with a semipermeable wall. The wall is applied by dipping it into the coating solution for 15 times, first for a 5 second dip, then for two 10 second dips, then for a 30 second dip and then for 1 minute per dip, with an intervening 5 minute drying period. Following the dipping the delivery dispenser is dried at room temperature, 72° F., about 22° C., for 5 days. The procedure applies about a 2 mm thick semipermeable wall. A passageway positioned by photo detection is laser drilled through the semi-permeable wall connecting the exterior of the dispenser with the heat sensitive drug formulation for releasing it at a controlled rate over time.

EXAMPLE 4

A dispensing system for delivering beneficial nutrients to warm-blooded ruminants is prepared as follows: first, a mold having a shape and configuration corresponding to the internal diameter and the hemispherical closed end of a capsule, is filled with an expandable density forming composition comprising 30 parts of ethyleneglycol monomethacrylate containing 0.12 parts of ethyleneglycol dimeth-acrylate, 10 parts of a 0.13% aqueous solution of sodium disulfate in aqueous ethanol, and 30 parts of iron powdor and magnesium. The composition polymerized at 30° C., and after 20 minutes following equilibrium to room temperature, the solid layer is removed from the mold. The solid expandable layer then is inserted, through the mouth of the capsule into the hemispherical area of the capsule. Next, the capsule is filled with a melted composition comprising 2.5% 1-lysine HCl, 1.5% DL-methionine, 21% glycergelatin and 75% theobromo oil, a glyceride of stearic acid, palmitic acid and lauric acid, to form on cooling to room temperature the thermo-responsive composition in laminar position with the expandable dense member. Next, the filled capsule is coated with a surrounding wall comprising cellulose acetate containing 10% polyethylene glycol 400. The semipermeable wall is applied in a pan type Hi-coater. The solvent used for forming the wall consists essentially of methylene chloride and methanol 95 parts by weight to 5 parts by weight. A 12 mil, 0.30 mm, thick wall of cellulose acetate butyrate is applied to the exterior surface of the capsule. Finally, a passageway is laser drilled through the semipermeable wall and the capsule wall communicating with the heat-responsive nutrient containing composition for its delivery to the environment of use.

EXAMPLE 5

A delivery device is made according to the procedure set forth in Example 1, with the conditions and materials as set forth, except that in this example, a varying rate controlling wall thickness comprising cellulose acetate butyrate and polyethylene glycol 400 is applied to the device. The thickness of the rate controlling wall varies from 30 mil (0.76 mm) at the end distant from the passageway in a uniform taper to 15 mil (0.38 mm) adjacent to the expandable density member.

EXAMPLE 6

A delivery device is prepared by following the procedures set forth above. The delivery device comprises a first compressed composition comprising 35 g of poly(ethylene oxide) having a molecular weight of 500,000; 30 g of iron powder and 5 g of sodium chloride, pressed against a second compressed composition comprising 38.5 g of neutral fat, 9.7 g of paraffin and 1.7 g of parbendazole. The laminated compressed layer are surrounded with a semipermeable wall that comprises 50% cellulose acetate butyrate, 45% poly(sulfone) and 5% citroflex citric acid ester selected from the group consisting of acetyl tributyl citrate and acetyl tri-2-ethylhexyl citrate. The device has a passageway through the semipermeable wall connecting the beneficial drug formulation with the exterior of the device.

EXAMPLE 7

A delivery system is made according to the procedure as set forth in Example 6, with all conditions as described except that the semipermeable wall comprises 80% cellulose acetate butyrate and 20% poly(sulfone), or 20% cellulose acetate butyrate and 80% poly(sulfone).

EXAMPLE 8

A series of delivery systems are prepared according to the procedures as set forth in Examples 6 and 7, with all conditions as described, except that in one embodiment 35 g of iron shot is used with the hydrogel; in another embodiment 80 g of iron shot is used with the hydrogel, and in another embodiment 120 g of iron shot is blended with the hydrogel to yield the respective delivery systems.

An embodiment of the invention pertains to (1) a method of increasing the deliverablity of beneficial agent by formulating a heat-sensitive composition containing a beneficial agent and (2) making the delivery system of the invention for increasing the deliverablity of the beneficial agent. An embodiment of the invention pertains also to a method for administering a beneficial agent at a controlled rate to the rumen of a ruminant, which method comprises the steps of: (A) admitting into rumen a dispensing device comprising (1) an outer wall formed of a polymeric composition permeable to the passage of fluid and substantially impermeable to the passage of drug, the wall surrounding (2) an internal lumen containing a layer of a beneficial drug formulation comprising a dosage unit amount of drug for performing a therapeutic program in a heat-sensitive pharmaceutically acceptable carrier that melts at body temperature and is a means for transporting the drug from the dispenser; (3) a layer of an expandable hydrogel in the lumen; said layer of an expandable hydrogel containing a density producing member for maintaining the dispenser in the rumen over a prolonged period of time, and, (4) an orifice through the communicating with the heat-sensitive drug formulation; (B) imbibing fluid through the wall at a rate determined by the permeability of the semipermeable wall and the osmotic pressure gradient across the semipermeable wall causing the layer of expandable hydrogel to expand and swell; (C) melting the drug formulation to form a flowable formulation; (D) delivering the beneficial drug formulation from the compartment by the expandable layer continually expanding against the melting formulation causing the formulation to be dispensed in a therapeutically effective amount through the orifice at a controlled rate to the rumen over a prolonged period of time; and (E) after the delivery period of the beneficial drug formulation the expandable hydrogel with density producing member 15 delivered causing a reduced system density thereby allowing the system to be passed from the immediate area and from the animal Inasmuch as the foregoing specification comprises preferred embodiment of the invention, it is understood that variations and modifications may be made herein in accordance with the inventive principles disclosed, without departing from the scope of the invention.

I claim:

1. A delivery system comprising:
   (a) a wall surrounding and defining an internal compartment, the wall comprising a composition permeable to the passage of fluid that enters the delivery system;
   (b) a beneficial agent in the compartment, said beneficial agent being a member selected from the group consisting of antibloat, anthelmintics, antibiotic, anti-infectious, antiparasitic, antimicrobial, and antiflea beneficial agents;
   (c) exit means in the wall for connecting the internal compartment with the exterior of the delivery system for delivering the beneficial agent from the delivery system;
   (d) means in the compartment for urging the beneficial agent through the exit means for delivering the beneficial agent over time; and,
   (e) a density member having a specific gravity of 2.2 to 7.6 and selected from the group consisting of iron, steel, iron-magnesium alloy, a mixture of cobalt and iron, copper oxide, iron oxide, and a mixture of copper oxide and iron comprising a specific gravity greater than the specific gravity of fluid that enters the delivery system blended in the means that urges the beneficial agent from the delivery system.

2. A delivery system according to claim 1, wherein the beneficial agent is mixed with a member selected from the group consisting of a glyceride having a melting point of at least 31° C., and a block copolymer of 1,2-butylene oxide and ethylene oxide.

3. A delivery system according to claim 1, wherein the means for urging the beneficial agent from the delivery system is a member selected from the group consisting of poly(ethylene oxide), poly(acrylamide), poly(acrylic acid), and poly(hydroxyalkyl acrylate).

4. A delivery system according to claim 1, wherein the means for urging the beneficial agent from the delivery system is a hydrogel.

5. A delivery system according to claim 1, wherein the means for urging the beneficial agent through the exit in the wall is a composition comprising a hydrogel and an osmotically effective solute that exhibits an osmotic pressure gradient across the wall.

6. A delivery system according to claim 1, wherein the means for urging the beneficial agent through the exit means in the wall comprises a hydrogel and a member selected from the group consisting of iron, steel, iron magnesium alloy, a mixture of cobalt and iron, copper oxide, iron oxide, and a mixture of copper oxide and iron.

7. A delivery system for delivering a beneficial agent according to claim 1, wherein the means for urging the beneficial agent through the exit means in the wall comprises a hydrogel, an osmotically effective compound that exhibits an osmotic pressure gradient across the wall, and a density producing member selected from the group consisting of iron, steel, iron magnesium alloy, a mixture of cobalt and iron, copper oxide, iron oxide, and a mixture of copper oxide and iron.

8. A delivery system according to claim 1, wherein the beneficial agent is replaced by a member selected from the group consisting of a nutrient, feed additive, vitamin, and drug.

9. A delivery system according to claim 1, wherein the beneficial agent is a member selected from the group consisting of albendazole, avermectin, cambendazole, fenbendazole, ivermectin, levamisole, morantel, mebendazole, oxybendazole, oxfendazole, parbendazole, parziquantel, thiabendazole, and techloroform.

* * * * *